United States Patent
Berry et al.

(10) Patent No.: US 7,322,474 B2
(45) Date of Patent: Jan. 29, 2008

(54) INTERACTIVE PRODUCT SELECTION SYSTEM

(75) Inventors: Lisa Berry, Ambler, PA (US); Frank Gualtieri, Warrington, PA (US); Jerry B. Hansen, Blue Bell, PA (US); Robert Hasselman, Lafayette Hill, PA (US)

(73) Assignees: McNeil-PPC, Inc., Skillman, NJ (US); Merck & Co., Inc., Rahway, NJ (US)

( * ) Notice: Subject to any disclaimer, the term of this patent is extended or adjusted under 35 U.S.C. 154(b) by 589 days.

(21) Appl. No.: 10/487,800

(22) PCT Filed: Oct. 18, 2002

(86) PCT No.: PCT/US02/33501

§ 371 (c)(1),
(2), (4) Date: Aug. 30, 2004

(87) PCT Pub. No.: WO03/036421

PCT Pub. Date: May 1, 2003

(65) Prior Publication Data

US 2005/0021413 A1 Jan. 27, 2005

Related U.S. Application Data

(60) Provisional application No. 60/337,448, filed on Oct. 22, 2001.

(51) Int. Cl.
*B65D 85/00* (2006.01)

(52) U.S. Cl. ............... 206/459.1; 116/284; 705/500; 434/429; 434/430

(58) Field of Classification Search ............ 206/459.1; 116/284; 434/429, 430; 705/500
See application file for complete search history.

(56) References Cited

U.S. PATENT DOCUMENTS 3,199,231 A * 8/1965 Ruderian .................... 434/404

(Continued)

FOREIGN PATENT DOCUMENTS

EP 0931732 * 7/1999

OTHER PUBLICATIONS

Allen, Jane, "medication errors abound at schools", Florida Times Union, Jan. 16, 2001.*
McLean, Donna, "Diatary instructions in the prescription drug regimens of a group of community dwelling older women: Indications, frequency, delivery characteristics and adherence", Michigan State University, 1995.*

*Primary Examiner*—Mark Fadok
(74) *Attorney, Agent, or Firm*—Connolly Bove Lodge & Hutz LLP

(57) ABSTRACT

The present invention involves an interactive selection system for a consumer product that improves the consumer's ability to quickly sort through numerous criteria in a complex decision making process and determine whether that particular consumer product is appropriate for his or her purchase and use. The interactive selection system is designed for a consumer product wherein the product is appropriate for less than all consumers comprising: (a) an interface; (b) at least one product selection device associated with the interface, wherein each product selection device is comprised of: (i) decision criteria that are relevant to appropriate selection or deselection of the product, (ii) at least two selectable responses associated with each decision criteria, wherein there is at least one positive selectable response and at least one negative selectable response for each decision criteria, and (iii) selection indicia associated with each selectable response; (c) directive instructions which direct an operator to manipulate each product selection device to choose a consumer applicable response from the available selectable responses per decision criteria; and (d) interpretive instructions which explain how to interpret the pattern of selection indicia which is observably associated with the chosen one or more consumer applicable responses to assist with determining whether or not the product is appropriate for the consumer's purchase or use.

16 Claims, 3 Drawing Sheets

U.S. PATENT DOCUMENTS

| | | |
|---|---|---|
| 3,571,947 A | 3/1971 | Maddison et al. |
| 3,638,603 A * | 2/1972 | Conover ..................... 116/308 |
| 4,155,326 A * | 5/1979 | Ellis ........................... 116/307 |
| 4,413,730 A * | 11/1983 | Morse ........................ 206/232 |
| 4,711,632 A * | 12/1987 | Detrick ....................... 434/106 |
| 5,520,203 A | 5/1996 | Segerstrom |
| RE35,445 E | 2/1997 | Pora |
| 5,758,095 A | 5/1998 | Albaum et al. |
| 5,848,976 A | 12/1998 | Weinstein |
| 5,984,685 A | 11/1999 | Portnoy |
| 6,093,027 A | 7/2000 | Unger et al. |
| 6,317,719 B1 | 11/2001 | Schrier et al. |
| 6,393,707 B1 * | 5/2002 | Maffei ....................... 33/1 SD |
| 6,488,202 B1 | 12/2002 | Seitz et al. |
| 6,692,436 B1 | 2/2004 | Bluth et al. |
| 6,926,904 B2 | 8/2005 | Slavtcheff et al. |
| 2001/0001144 A1 | 5/2001 | Kapp |
| 2002/0029223 A1 | 3/2002 | Rice et al. |
| 2003/0069002 A1 | 4/2003 | Hunter et al. |

* cited by examiner

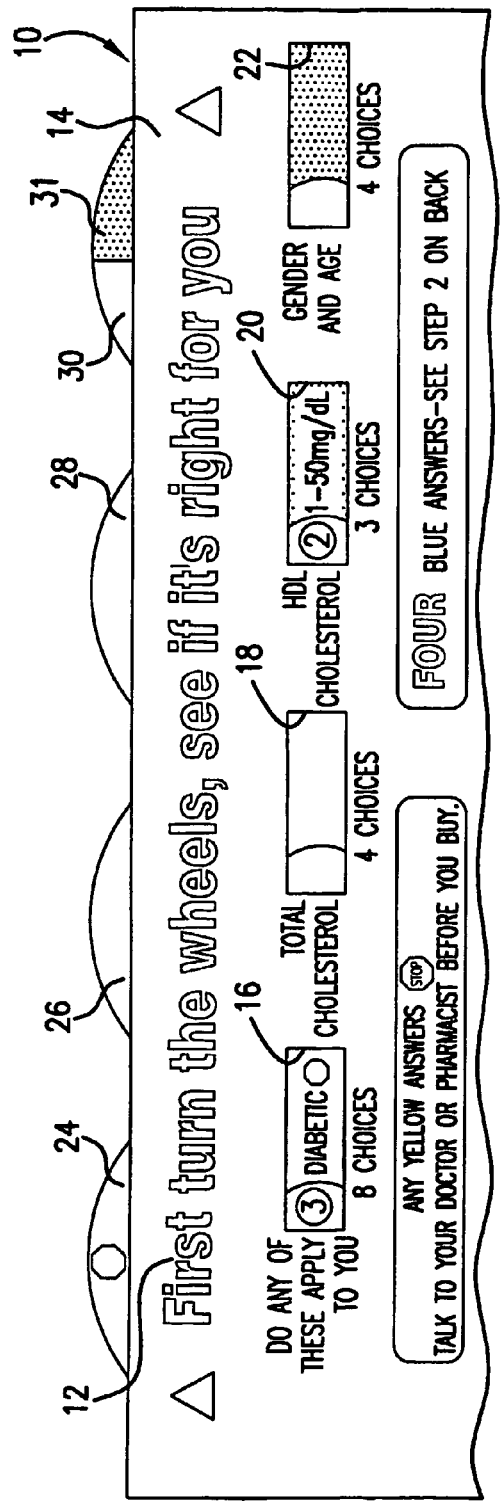
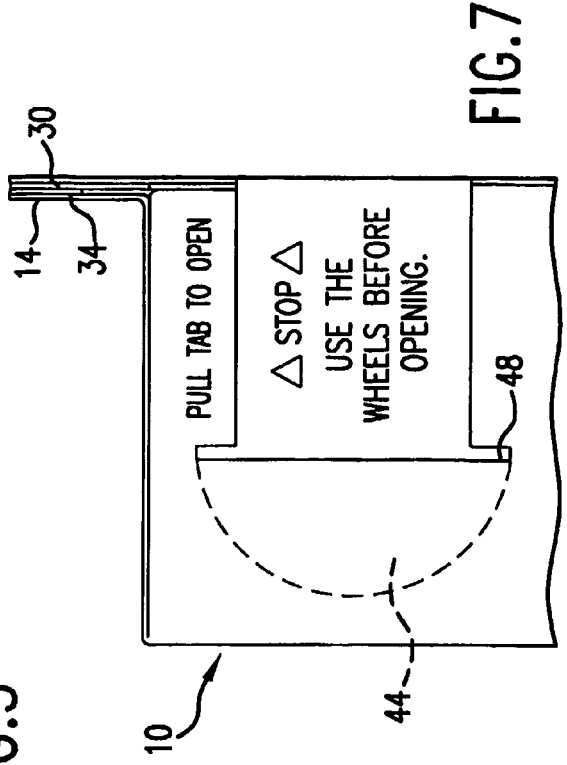

INTERACTIVE PRODUCT SELECTION SYSTEM

CROSS REFERENCE TO RELATED APPLICATION

This application is a national stage application (under 35 U.S.C. 371) of PCT/US02/33501 filed Oct. 18, 2002, which claims the benefit of U.S. provisional application Ser. No. 60/337,448 filed 22 Oct. 2001.

BACKGROUND OF THE INVENTION

Several consumer products, particularly over-the-counter (OTC) pharmaceuticals, require careful consideration before purchase. Consumption of such products without proper screening has the potential for adverse affects on the consumer or can cause ill will toward the seller if the product is ineffective in treating the consumer's condition.

Despite the recent increase in television and print advertising of pharmaceuticals and conditions treated by them, consumers still lack knowledge about the appropriateness of certain pharmaceuticals for their use. The same is true of other consumer products which require selection at the point of sale.

Various attempts have been made to assist this consumer selection of products. For example, Unger, et al. U.S. Pat. No. 6,093,027, describes a system for selection from among hundreds of feminine hygiene products of that which is best suited for a given consumer. In preferred embodiments of this patent, the collection of information from a consumer and the selection of a system of feminine hygiene products may be performed using a computer, World Wide Web, an interactive display, a telephone system, published questionnaires, or through literature distributed to health care providers (column 15, lines 1-29). The packaging described in the Unger, et al. patent merely identifies, e.g., by package color, which product corresponds to the various systems selected by the customer on the computer, web, etc.(column 15, lines 29-44).

Another consumer selection system is described in Segerstrom U.S. Pat. No. 5,520,203. This patent describes a process that generally comprises the steps of determining the prospective user's hair color, skin color, skin type, etc., and making a recommendation regarding cosmetics using a decision tree (see FIG. 2 therein). The recommendation corresponds to a tailored kit containing a complete set of cosmetics for the user's type. The decision tree can be part of an order form in a mail-order catalogue, or an in-store display including a poster or electronic display (col. 3, lines 20-26; col. 6, lines 51-53).

Weinstein U.S. Pat. No. 5,848,976 discloses a 3-part system combining graphical indicia and medicinal dosages, in which a patient is presented with written questions regarding allergenic substances and conditions (step 1), then provided recommendations regarding allergen avoidance (step 2), followed by provision of allergy medicine in timed dosages (step 3). A permanent record is created when the patient is treated using this system. While the disclosure states that, "step 3 provides at least one sequential array of dosage units, which effect a medication regimen that is timed as a function of steps 1 and 2," (col. 2, lines 44-47), there does not appear to be any interactive decision making within this process. The same medication is dispensed to the patient as part of a total package, regardless of the outcome of steps 1 and 2.

Other pharmaceutical packaging currently available typically contains printed text thereon describing dosage information, side effects and drug interaction information. More detailed information on these topics is typically included in package inserts. However, the suitability of the packaged pharmaceutical for a particular consumer's health condition is typically not readily evident from the packaging without extensive scrutiny. There is currently no process that allows potential consumers to input personal information pertinent to the condition treated by the consumer product and receive feedback on whether or not to purchase that product.

Consumers are presented with an ever-increasing amount of information regarding consumer products, with many complex factors that need to be considered in order to make a correct purchase decision. Consumers need help in making these complex purchase decisions, and/or guidance directing them to contact a more knowledgeable third party or expert to address their needs if it turns out that the product is not appropriate for them. For example, in the selection of over-the-counter pharmaceuticals, consumers must consider many factors to determine whether that medicine is right for them. The potential for unwanted side effects from an improperly selected medicine exists, as well as the risk that their condition will not be adequately treated. Also, a flawed selection process can result in a waste of the consumer's money or ill-will toward the seller if the medicine doesn't work.

The present invention addresses this need.

SUMMARY OF THE INVENTION

The present invention involves an interactive selection system for a consumer product that improves the consumer's ability to quickly sort through numerous criteria in a complex decision making process and determine whether that particular consumer product is appropriate for his or her purchase and use. This interactive selection system for a consumer product preferably offers a visible and prominent display that allows potential consumers of the product to input personal information at the point of sale and obtain specific feedback on whether the consumer product is appropriate for the consumer.

The invention informs the consumer whether or not they should purchase the consumer product based on each consumer's set of personal characteristics. The invention has the distinct advantage of helping a consumer focus on the factors of greatest importance from all the information available concerning a given product, making the information easier to comprehend and use toward making a correct purchase decision. It has the further advantage of providing a clear and definitive answer regarding whether or not the product is appropriate for purchase or use by that consumer. It also permits a very quick and accurate purchase decision without first having to read paragraphs of print copy on, or inside, the package. Most present day consumers are pressed for time and therefore unwilling, or unlikely, to spend the time needed to read extensive copy as a predicate to their purchase decision.

One object of the present invention is to provide an interactive selection system for a consumer product wherein the product is appropriate for less than all consumers comprising:

(a) an interface;

(b) at least one product selection device associated with the interface, wherein each product selection device is comprised of:

(i) decision criteria that are relevant to appropriate selection or deselection of the product, (ii) at least two selectable responses associated with each decision criteria, wherein there is at least one positive selectable response and at least one negative selectable response for each decision criteria, and (iii) selection indicia associated with each selectable response;

(c) directive instructions which direct an operator to manipulate each product selection device to choose a consumer applicable response from the available selectable responses per decision criteria; and (d) interpretive instructions which explain how to interpret the pattern of selection indicia which is observably associated with the chosen one or more consumer applicable responses to assist with determining whether or not the product is appropriate for the consumer's purchase or use.

Another object is to provide a method for assisting a consumer with determining whether or not a consumer product is appropriate for their purchase or use comprising:

(a) observing one or more decision criteria that are relevant to appropriate selection or deselection of the product, wherein each decision criteria is associated with at least two selectable responses and at least one of the selectable responses is a positive selectable response and at least one of the selectable responses is a negative selectable response per decision criteria, and wherein each positive selectable response is associated with an observable positive selection indicia and each negative selectable response is associated with an observable negative selection indicia;

(b) choosing a consumer applicable response for each decision criteria from the selectable responses associated with each decision criteria;

(c) observing the pattern of selection indicia observably associated with the chosen one or more consumer applicable responses;

(d) reading interpretive instructions which explain how to interpret the pattern of selection indicia regarding whether or not the product is appropriate for purchase or use by the consumer; and (e) interpreting the pattern of selection indicia to determine whether or not the product is appropriate for purchase or use by the consumer.

Additional objects will be evident from the following detailed description.

DESCRIPTION OF THE DRAWINGS

The accompanying drawings, which are incorporated in and constitute a part of this specification, illustrate embodiments of the invention, and together with the description to explain the principles of the invention. In the drawings:

FIG. 5 is a fragmented front elevational view of the packaging illustrating typical instructional text on the packaging to be used in conjunction with decision wheels;

FIG. 6 is a side cross-sectional view in elevation of the decision wheel and packaging taken along line 6-6 of FIG. 1; and FIG. 7 is a fragmental right side elevational view of a portion of the packaging illustrating closure flaps used on the packaging and typical instructional text thereon.

DETAILED DESCRIPTION OF THE INVENTION

Figure 1:
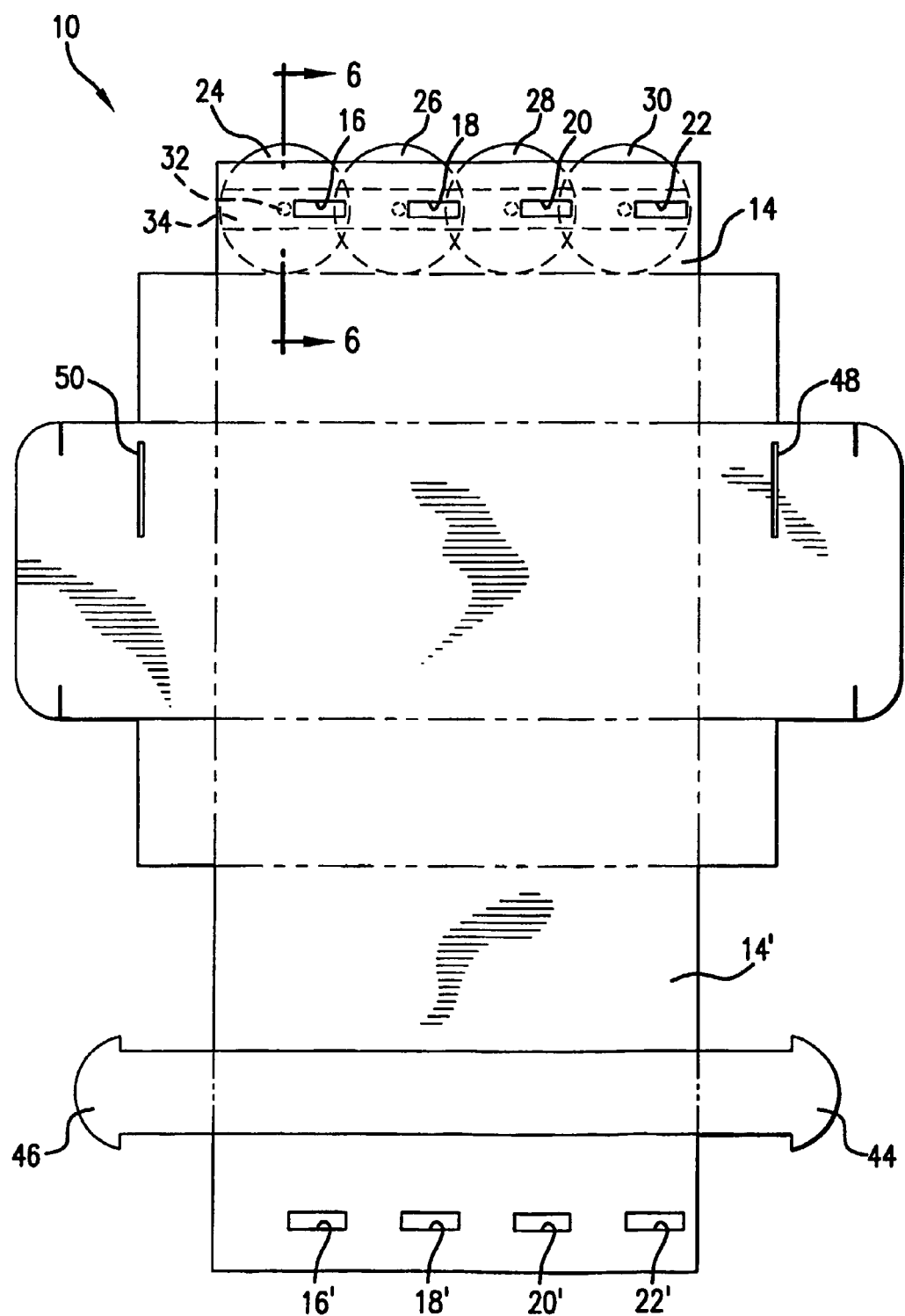
FIG. 1 is top plan view of the interactive packaging of this invention in an unassembled condition.

Reference will now be made in detail to the following described embodiments of the invention, examples of which are illustrated in the accompanying drawings. The interactive selection system of the present invention is intended for use with consumer products that are appropriate for use by some but not every consumer. The term "consumer" as used herein is intended to mean the person whose personally applicable responses are chosen from the available selectable responses in the interactive selection system. The consumer is the person for whom the decision must be made regarding whether or not the product is appropriate. The term "operator" refers to the person who actually manipulates the interactive selection system using the consumer's personal information in order to choose one selectable response per decision criteria. Preferably, the operator and the consumer are the same person, but the operator can be a different person who assists the consumer with the interactive selection system, such as a companion, or someone with specialized knowledge with respect to the particular product, such as a technical expert or a doctor, pharmacist, nurse or other caregiver.

The term "consumer product," as used herein, is intended to include goods bought for personal use. Several consumer products, particularly OTC pharmaceuticals, require consideration of certain criteria before a decision can be made as to whether or not the product is appropriate for use by an individual consumer. For example, for OTC pharmaceuticals, the product may be inappropriate for use by children under a stated age, or for those suffering with certain medical conditions or taking specific contra-indicated medications. However, absent any disqualifying criteria, the product may be appropriate and desirable for other consumers. The interactive selection system of the present invention assists the consumer in making the correct decision regarding whether or not to purchase (whether making an initial purchase or a re-purchase) and use the consumer product based on personal information that is relevant to selection or deselection of the product. Thus the present invention provides an interactive selection system for a consumer product wherein the product is appropriate for less than all consumers which includes an interface, at least one product selection device associated with the interface, directive instructions which direct an operator, which can be the consumer himself, to manipulate each product selection device to choose a consumer applicable response from the available selectable responses per device and interpretive instructions which explain how to interpret the pattern of selection indicia which is observably associated with the chosen one or more consumer applicable responses after a consumer applicable response has been chosen for each device, to assist with determining whether the product is appropriate or inappropriate for the consumer's purchase or use.

The term "observable" (and forms thereof such as "observably," "observing," etc.) is intended to have its common meaning, i.e., perceptible (or "perceptibly," perceiving," etc. as appropriate) using any one or more of the five human senses, e.g., sight, sound, touch, taste and smell. The system described herein can employ interaction with one or more of the five senses, and particularly may employ visual, audible and tactile interaction or combinations thereof.

The term "interface", as used herein, is intended to be a tangible point of interaction between the interactive selection system and a human operator. More particularly, the interface provides a platform for the operator to interact with and manipulate the product selection devices, and can be a platform for electronic or non-electronic interaction. For example, the interface could be the packaging which is an enclosure for the product, such as a paperboard box or carton, which contains the product wherein the product selection devices are integral with the packaging. Alternatively, the interface could be one that is separate from the product and its packaging such as, for example, a stationary interface available at the product's point of sale, or a mobile interface that is independent of the packaging or a point of sale display and is transportable, for example an interface fabricated from paper or plastic that is pocket-sized. The interface could also be a hybrid stationary/mobile interface that is releaseably attached, for example, to the product package or a point of sale display but is capable of being disassociated from the packaging or the display for mobile use. An interface also includes a computer interface wherein a desktop or portable monitor screen or a hand-held device screen (e.g., a personal digital assistant) serves as a platform for the electronic presentation of the product selection devices on the screen.

The "product selection device" is a mechanism which can be manipulated comprised of decision criteria that are relevant to appropriate selection or deselection of the product, at least two selectable responses associated with each decision criteria, and selection indicia associated with each selectable response. Product selection devices can exist in both electronic and non-electronic formats. Examples of product selection devices include, but are not limited to rotatable decision wheels, slide rule type devices and the like that convey decision criteria, selectable responses and selection indicia, as well as observable electronic representations of the decision criteria, selectable responses and selection indicia, and combinations thereof. For example, rotatable decision wheels or slide rules could be non-electronic fabrications as they have been classically known, or electronic representations of a decision wheel or slide rule could be displayed on a computer monitor where the operator uses a cursor to spin (or drag) electronically moveable portions of the image to reveal and/or choose selectable responses. In another example, the product selection device is presented textually in electronic format and the operator simply reads each decision criteria and electronically selects a consumer applicable response for each decision criteria, whereupon a pattern of selection indicia will be observable. Any type of design, either electronic or non-electronic, which functions as a product selection device as described herein is encompassed by the instant invention.

The "decision criteria" will have relevance to the decision-making process for deciding whether or not a product is appropriate for, and therefore could be purchased and used by, a consumer considering using the product. Since different criteria for use will apply to different products, the decision criteria will vary depending on the product being marketed. Examples of decision criteria include but are not limited to characteristics such as age, gender, pregnancy, nursing, total cholesterol level, high density lipoprotein (HDL) cholesterol level, low density lipoprotein (LDL) cholesterol level, pre-existing medical conditions, daily lifestyle habits such as alcohol intake over a specified period of time, blood pressure, medical indicators, allergies, drug sensitivities, concurrent medications including prescription and non-prescription medications, and combinations thereof. Examples of preexisting physical and medical conditions include, but are not limited to pregnancy, obesity, body mass index, heart disease, cardiovascular disease, angina, heart attack, stroke, diabetes, insulin resistance, hypertension, metabolic syndrome, anorexia, bulimia, liver disease, hepatitis and the like, and combinations thereof. Examples of medical indicators include, but are not limited to levels of triglycerides, apolipoproteins, Lp(a), C-reative protein (CRP), blood sugar, bone structure, bone density, family history, history of bone fractures, race, and the like and combinations thereof. A decision criteria for a product selection device could include a group of characteristics any one of which would be incompatible with appropriate use of the product, such as a group of physical and medical conditions, lifestyle habits and concurrent medication usage.

For the sake of brevity, the term "criteria" as used herein includes both single (i.e., criterion) and multiple (i.e., criteria) characteristics on which a decision may be based. Therefore, a decision criteria associated with a product selection device may include single or multiple characteristics which are relevant to the decision making process. For example, decision criteria associated with a single product selection device may be, for example, a single criterion of age, or multiple criteria of age and gender. Generally, the decision criteria associated with a single product selection device will be one or two characteristics, but combinations of more than two characteristics per device can be used when appropriate, for example as described above when there is a group of characteristics any one of which would be incompatible with appropriate use of the product.

The term "selectable responses" are the answers that are associated with each decision criteria. There must be at least two selectable responses per product selection device in order to let the operator choose a consumer applicable response (or where the operator is the consumer, then to let the consumer pick a personally applicable response) in light of the decision criteria associated with a given product selection device. For example, if the decision criteria for a given product selection device is age, then example selectable responses may include "50 years and over" and "under 50 years", or "under 18 years," "18 to 35 years," 36 to 55 years" and "56 years and over." As another example, if the decision criteria for a given product selection device is age and gender, then an example group of selectable responses could include "male under 55 years," "male 55 years and older," "female under 55 years," and "female 55 years and older." In another example, the decision criteria could be stated as a "yes or no" answerable question such as "Are you over 50?" where the selectable responses would be "Yes" and "No."

The group of selectable responses associated with a particular decision criteria should together be comprehensive, that is, they should as a group cover every answer possibility so that every consumer will be able to choose at least one as a consumer applicable response. Depending on the decision criteria, selectable responses can be used such as "I don't know" (for example when the decision criteria is HDL cholesterol level) or "None of the other answers apply to me" (for example when the decision criteria is group of characteristics any one of which would be incompatible with appropriate use of the product) in order to achieve a comprehensive group of selectable responses.

Manipulation of the product selection device by an operator to choose a consumer applicable response can be accomplished by any suitable means in light of the design of the interface and product selection devices, and is not limited to manual manipulation. For example, the product selection device could be manipulated by spinning a rotatable decision wheel, sliding the moveable portion of a slide rule, lifting a flap, or any other type of manual manipulation of the device. Alternatively, the product selection device could be manipulated using a keyboard, mouse, track ball, stylus, finger-touch, sound such as voice, bar-code reading device or any other method which is compatible with the format of the product selection device and is capable of selecting a consumer applicable response.

Each of the selectable responses will be either positively associated with appropriate purchase and use of the product by a consumer (i.e., a positive selectable response), or negatively associated with appropriate use (i.e., a negative selectable response) and therefore would be associated with deselection of the product. At least one of the selectable responses for each decision criteria must be positively associated with appropriate purchase and use of the product, and at least one of the selectable responses must be negatively associated with appropriate purchase and use and therefore would be associated with deselection of the product.

The terms "personally applicable response" and "consumer applicable response" will both be used interchangeably herein to refer to the selectable response that is chosen from among the available selectable responses associated with a product selection device and that applies to the consumer who is deciding whether or not to purchase or use the product. The term "personally applicable response" is generally used herein when the consumer is the operator.

The term "selection indicia" is intended to mean any observable symbol which is either positively associated with appropriate purchase and use of the product, i.e., positive selection indicia, or negatively associated with appropriate purchase and use of the product, i.e., negative selection indicia. Selection indicia include observable symbols such as graphic symbols including color coding, alphanumeric graphics, pictorial graphics and the like, and sounds such as musical notes, bells, audible language and the like, and combinations thereof. The selection indicia is chosen to be compatible with the design of the interface and product selection devices. Graphic symbols are preferred, particularly for product selection devices in non-electronic format. Each selectable response that is positively associated with appropriate purchase and use of the product is assigned a positive selection indicia, and each selectable response that is negatively associated with appropriate purchase and use of the product is assigned a negative selection indicia. While the selection indicia associated with a selectable response may or may not be observable prior to selection of a consumer applicable response, it must be observable upon selection of the response as a consumer applicable response.

Since each selectable response will be associated with a selection indicia, there will be an equal number of selectable responses and selection indicia in a given interactive selection system. Generally, an "opposite pair of selection indicia" comprised of one positive selection indicia and one negative selection indicia is chosen for use with a system, wherein the positive and negative selection indicia are repeatedly associated with each of the selectable responses as appropriate. For example, an opposite pair of selection indicia could be comprised of (a) the color green or a green background coupled with the word "Yes" as the positive selection indicia, and (b) the color red or a red background coupled with the word "No" as the negative selection indicia, wherein the positive selection indicia defined in part (a) is repeatedly associated with each of the positive selectable responses in the system, and the negative selection indicia defined in part (b) is repeatedly associated with each of the negative selectable responses in the system. Any opposite pair of selection indicia can be used with a system, including but not limited to other color pairs, graphic representations of a "Stop" sign and green traffic light, textual and/or audible "Stop" and "Go," a thumbs up and thumbs down graphic, an audible bell and buzzer, and the like, as well as combinations thereof. The opposite pair of selection indicia, as the term is used herein, are defined as two different selection indicia having opposite meanings (i.e. positive and negative) within the context of an individual interactive selection system; the pair need not be recognized as having opposite meanings when viewed apart from the interactive selection system, and could also be, for example, a star and a moon, the colors blue and yellow, and the like.

For the sake of brevity, the term "indicia" as used herein includes both single symbols (i.e., indicium), such as a single color or graphic, and combinations of symbols (i.e., indicia), such as stripes of alternating colors or a specific color background with a pictorial and/or alphanumeric graphic in the foreground, and the like. Therefore, a single selection indicia may be comprised of one symbol or a combination of symbols which, when observed together as a whole, serve as a single positive or negative selection indicia.

Whenever possible, the selectable responses associated with a decision criteria should be drafted to be mutually exclusive for the decision criteria, i.e. there would be one, but only one, correct consumer applicable response among the selectable responses. For example, if the decision criteria is age and the selectable responses are age ranges as exemplified above, there will be only one correct answer for each consumer. However, when the selectable responses cannot be drafted to be mutually exclusive, such as when the decision criteria are a combination of characteristics any one of which would be incompatible with appropriate use of the product (therefore resulting in the possibility that more than one characteristic could apply to a consumer and therefore more than one response could be chosen), then the selectable responses that are non-exclusive of each other must all have the same selection indicia, whether it be positive or negative (referred to herein as selection indicia no. 1). There also must be at least one selectable response that is associated with the opposite selection indicia (referred to herein as selection indicia no. 2) and is exclusive of the responses associated with selection indicia no. 1. For example, if the decision criteria is a combination of characteristics any one of which would be incompatible with appropriate use of the product, an example group of selectable responses could include "heart disease," "liver disease," "pregnant" and "none of these conditions." The first three listed responses are non-exclusive of each other since a consumer could have all three conditions, while the last listed response is exclusive from the first three responses because it cannot accurately be chosen together with any of the first three responses. In this example, the first three listed responses would all be associated with the same negative selection indicia, while the last listed response would be associated with an opposite, positive selection indicia. Therefore, the same ultimate pattern of selection indicia will be observable whether the consumer chooses "heart disease," "liver disease," or "pregnant", and applying the interpretive directions to the pattern of selection indicia will result in the same outcome regardless of which of these non-exclusive responses is chosen.

"Directive instructions" are used to direct the operator to manipulate each product selection device in order to select a consumer applicable response from the available selectable responses in light of the decision criteria that are associated with each device. The directive instructions can be any text and/or graphic, such as an arrow, which draws attention or invites the operator to manipulate the product selection device(s) in order to choose consumer applicable responses. For example, if the consumer is 55 years old and the decision criteria for a product selection device is age, and the selectable responses are "under 50 years" and "50 years and older," the operator, who can be the consumer himself, would choose the latter response. In order to direct the operator to choose a consumer applicable response, the directive instructions could, for example, generally state "Select The Responses That Are Right For You" along with the word "Age" adjacent to the product selection device and similar statements as to other decision criteria adjacent to other devices. Alternately, a question or directive could be associated with each device in the system, such as "What is your age?", "Choose your Gender", "Do you have any of the following medical conditions?" etc. Any combination of words or graphics which directs the operator to interact with the product selection devices and thereby choose consumer applicable responses is within the scope of this invention. While the directive instructions are associated with the instant interactive selection system, they may be integrated on the same interface that the product selection devices are associated with, or the directive instructions may be presented on a different interface. For example, the directive instructions may be displayed on the product package and direct the operator to manipulate product selection devices on a point-of-sale display. Preferably, the directive instructions are integrated on the same interface that the product selection devices are associated with, for example the product packaging.

Once a selectable response has been chosen as a consumer applicable response for each product selection device in the system, selection indicia will be observably associated with each consumer applicable response. "Interpretive instructions" are then necessary to explain how to interpret or draw a conclusion regarding whether or not purchase or use of the product is appropriate for a particular consumer based on the pattern of selection indicia that is associated with the consumer applicable responses. While the interpretive instructions are associated with the instant interactive selection system, they may be integrated on the same interface that the product selection devices are associated with, or the interpretive instructions may be presented on a different interface. For example, the interpretive instructions may be displayed on the product package while the product selection devices are on a point-of-sale display. Preferably, the interpretive instructions are integrated on the same interface that the product selection devices are associated with, for example the product packaging. More particularly, the directive instructions, interpretive instructions and the product selection devices associated with the interactive selection system are all integrated with the same interface.

As used herein, the phrase "pattern of selection indicia" refers to the group of selection indicia observably associated with the consumer applicable responses for an individual consumer after the operator has chosen one selectable response per product selection device in the interactive selection system. The pattern of selection indicia can be comprised of one selection indicia (when the system has only one product selection device) or a group of two or more selection indicia (when the system has two or more product selection devices), wherein each selection indicia in the group is either positive or negative and is associated with a consumer applicable response. The pattern of selection indicia which leads toward a determination of whether or not the product is appropriate for use will vary with the product, and with the choice of decision criteria, selectable responses and selection indicia incorporated into the system. For example, if the selection indicia for a system were a pair of colors such as green and red (as exemplified above) and the system had four product selection devices, the interpretive instructions could state: "If all of your answers are green, this product is right for you. If any of your answers are red, do not use this product." An alternate example could be: "If at least three of your answers are green, this product is right for you." In these examples, the pattern of selection indicia for individual consumers could vary from four red color codes to four green color codes to any combination of red and green color codes totaling four.

The interpretive instructions may also optionally advise the consumer that, based on the pattern of selection indicia associated with their personally applicable responses, additional action must be taken or information obtained in order to make a correct final decision. In a case where the interpretive instructions specify such further action, the effect of the interactive selection system is to provide a first step in the decision tree process of deciding whether or not the product is appropriate for the consumer. For example, if a healthcare product is involved and the pattern of observable selection indicia indicates the product may be inappropriate for the consumer, the interpretive instructions could inform the consumer not to purchase or use the product, or alternatively could inform the consumer to seek the advice of a health professional, such as a pharmacist or other medical caregiver, before purchasing or using the product. The concept conveyed by informing the consumer to seek the advice of a health professional (or other knowledgeable person) before purchasing or using the product is not intended to mean that the consumer should consult a health professional and then purchase or use the product. Rather, such interpretive instructions are intended to convey that the consumer should rely on the advice of the health professional for determining the course of treatment and/or types of products that the consumer requires to address his needs, which may or may not include use of the originally considered consumer product. As another example, if the pattern of observable selection indicia indicates the health care product might be appropriate for the consumer, the interpretive instructions could inform the consumer to continue reviewing additional label information about the product before making a final decision to purchase or use the product.

The decision criteria chosen to be used with a given consumer product can be the basis for providing a definitive answer regarding whether the product is appropriate or not for use by the consumer, so that certain responses to decision criteria which must be met in order to appropriately use the product or which would preclude use of the product are addressed by the system. Accordingly, depending on the pattern of selection indicia which results after all responses are chosen, the directive instructions could convey that either the product is appropriate for purchase and use by the consumer, or the product is not appropriate. When the system conveys that the product should not be purchased or used by the consumer, this system has the additional ability to use the directive instructions to direct the consumer to consult someone with specialized knowledge with respect to the particular product to seek additional information or advice, such as a technical expert or a doctor, pharmacist, nurse or other caregiver. This is particularly advantageous when the consumer product is an OTC pharmaceutical, and the consumer has chosen one or more negative selectable responses that may warrant further professional medical attention.

Any interpretive instructions can be used which explain how to interpret the pattern of selection indicia associated with the personally applicable responses to assist the consumer in making a correct purchase or use decision, and the examples provided herein are not intended to limit the various ways that interpretive instructions can be drafted. It is preferred that the consumer use the interactive selection system in order to make an informed decision regarding whether or not to initially purchase the product, but purchase of the product followed by manipulation of the interactive selection system to determine if the consumer's use of the product is appropriate or not is also within the scope of this invention.

The interactive consumer product selection system may be integral with or releasably associated with point of sale displays, retail kiosks, product packaging and the like, or it may also be presented in electronic form at to be available at the point of sale or remotely via computer terminals, hand-held electronic devices, and the like, and combinations thereof. The interactive consumer product selection system can be a mobile system that is separate from the point of sale or product packaging, for example for use by doctors, nurses, pharmacists or other clinicians and caregivers to assist a consumer in making a purchase decision.

In accordance with one embodiment of the present invention, the interactive consumer product selection system comprises an interactive package having product selection devices in the form of "decision wheels" built into the packaging. The package contains multiple windows that frame information (i.e., selectable responses and associated selection indicia) on the decision wheels that are positively or negatively associated with use of the consumer product relative to personal information about the consumer. Each decision wheel is associated with a decision criteria that is relevant to whether or not the product is suitable for an individual consumer. More particularly, each decision wheel is rotated until a selectable response on a wheel corresponds to the consumer's individual condition or characteristic, for example, his or her age, sex, or health condition. The pattern of selection indicia, for example coloration or symbols, viewable through the windows on the decision wheels after the consumer applicable responses are chosen indicates whether or not the consumer product is appropriate for that consumer based on the information provided in the interpretive instructions, which are printed on the product package. Typically, multiple decision wheels are used for the package so that multiple decision criteria can be addressed by the consumer. For example, a first wheel might address the consumer's age and sex, a second wheel might list health conditions which militate against use of the product and a third wheel might list ranges of health criteria (cholesterol, blood pressure, etc.) which can or cannot be effectively treated by the product. If after selection of consumer applicable responses all of the decision wheels display positive selection indicia in the window frames of the packaging, as determined by applying the interpretive instructions, the consumer would then have an immediate visual indicator that the product is the right one for him or her. This represents a substantial improvement in clarity and time reduction over prior methods of textual or pictorial guidance of the consumer's purchase decision.

One application of this invention includes but is not limited to the packaging of OTC medicines, such as for the management of lipid levels and particularly for treatment of elevated cholesterol levels, arthritis, emergency contraception, hair loss, pediculosis, hypertension, migraine, muscle relaxants, overactive bladder/urinary urge incontinence, urinary tract infections, osteoporosis, high blood pressure, asthma, colds, flu, pain or any other medical conditions which are or eventually become treatable with OTC products. For example, compounds known as 3-hydroxy-3-methylglutaryl coenzyme A (HMG-CoA) reductase inhibitors or "statins" are currently known to be effective prescription cholesterol lowering medicines, but may eventually become available over-the-counter. Examples of statins include but are not limited to lovastatin, simvastatin, pravastatin sodium, atorvastatin calcium, fluvastatin sodium, as well as salt forms of rosuvastatin and pitavastatin. In addition to statins, other lipid-modifying agents may become OTC medications such as cholesterol absorption inhibitors, for example ezetimibe, and can be employed with the instant invention.

Other examples of pharmaceutically active agents include, but are not limited to COX-2 inhibitors such as rofecoxib; bisphosphonates for the treatment and prevention of osteoporosis such as alendronate sodium and risendronate; angiotensin converting enzyme inhibitors for treating high blood pressure such as enalapril, lisinopril and captopril; angiotensin II antagonists such as losartan potassium and losartan potassium-hydrochlorothiazide; asthma medications such as montelukast sodium; anti-muscarinic agents for treatment of overactive bladder/urge urinary incontinence such as oxybutynin chloride and tolterodine; protriptyline, HCl; desogestral; norethindrone/ethinyl estradiol; norgestimate/ ethinyl estradiol 17 (beta)-estradiol/micronized norgestimate; estropipate; 5-alpha reductase inhibitors such as finasteride; ivermectin; rizatriptan; cyclobenzaprine HCl; norflaxacin; rabeprazole, omeprazole and lansoprazole; and the like and combinations thereof.

Combinations of two or more pharmaceutically active agents are also encompassed by the instant invention where each active agent is in a separate dosage unit or combined in a single dosage unit. For instance, a statin can be combined with another lipid-modifying agent, e.g., simvastatin with ezetimibe.

Consumers are generally aware from television, print media, or their health care provider that the above-described examples of health risk can be corrected with medication. Many consumers are therefore interested in OTC medicines to treat these conditions. However, these products are not appropriate for everyone. Thus, with regard to the treatment of elevated cholesterol levels, some consumers have total cholesterol levels that may be too low or too high for treatment with a particular dosage amount of a statin or have an exclusionary medical condition such as hepatitis or other liver disease. This invention facilitates consumer determination of who can safely benefit from a consumer product, and particularly OTC medicines.

EXAMPLE

In one preferred embodiment of this invention, the interactive selection system is an interactive consumer product package which is a paperboard carton that includes multiple (typically 2-6) "decision wheels" integrated with the package. For each decision wheel there is a decision criteria, and there is a window in a portion of the package. The selectable responses and their associated positive or negative selection indicia are arrayed on the decision wheel. Each decision wheel is rotatably attached to the packaging behind a window that displays the selectable responses and associated selection indicia. The selectable responses and associated selection indicia are arrayed on each wheel so that one selectable response is visible at a time through the window as the wheel is turned.

The "decision wheel" is the rotatable wheel having an array of selectable responses with associated positive and negative selection indicia, as illustrated in FIGS. 1, 2, 4 and 5 as elements 24, 26, 28 and 30. In this embodiment, each product selection device is intended to encompass a system for selecting a consumer applicable response comprised of the decision wheel, the window from which the selected response can be viewed, and the decision criteria associated with the selectable responses. The interactive selection system of this embodiment is comprised of the directive instructions and interpretive instructions which appear on the product packaging in addition to the product selection devices described above.

In a specific example of this embodiment where the consumer product would be OTC MEVACOR® (lovastatin), four windows and related decision wheels illustrate four decision criteria, namely: (1) age and gender of the consumer; (2) the consumer's total cholesterol level; (3) the consumer's HDL cholesterol level and (4) health and lifestyle characteristics that counsel against usage. The selectable responses and positive and negative selection indicia associated with each response are contained in radial segments on rotatable wheels behind the windows. Directive instructions appear on the packaging directing the operator to turn each wheel to display through each window a consumer applicable response in view of the decision criteria for each decision wheel. Interpretive instructions also appear on the packaging which explain that if any window displays a pre-determined negative selection indicia, then the consumer should not buy or use the product without first consulting a person knowledgeable with appropriate use of the product, or if all the windows show pre-determined positive selection indicia then the product may be appropriate for their purchase and use but the consumer should read further label information to be sure.

Figure 4:
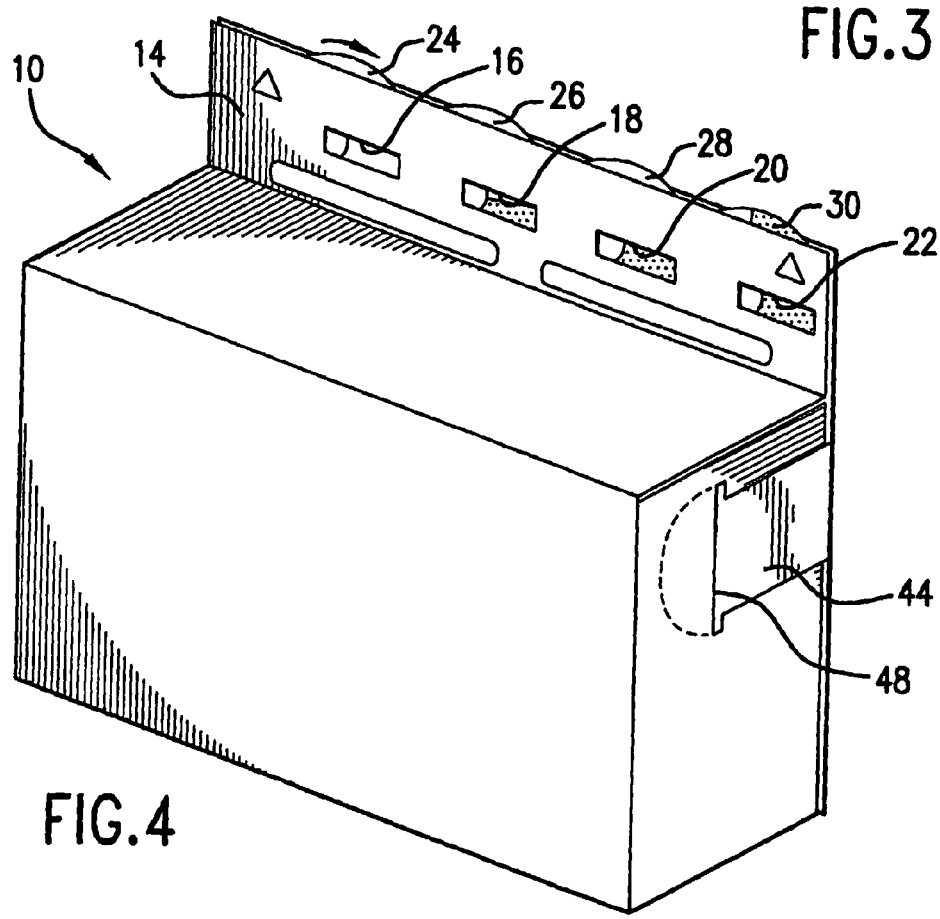
FIG. 4 is a perspective view of the assembled packaging of this invention.

As previously stated, a consumer selecting an over-the-counter medicine preferably has all the information needed to make that selection presented to him or her on the packaging in an easy-to-use format. FIGS. 1 and 4 illustrate packaging of this invention 10 which presents information for a cholesterol reducing medicine in a unique interactive format using decision wheels. The invention, of course, has application to a wide range of products that require consumer choice regarding whether or not a particular product is personally appropriate for purchase and use, not just pharmaceuticals.

A consumer in the market for an OTC medicine, for example to reduce and control cholesterol, would approach the store shelf where the interactive package is displayed. As illustrated in FIG. 5, the consumer would be immediately alerted to the decision criteria for selection or deselection of the product by the directive instructions of legend 12 in an upstanding back panel 14 of package 10 to the effect "FIRST TURN THE WHEELS, SEE IF IT'S RIGHT FOR YOU." As can be seen in FIGS. 1 and 4, panel 14 contains multiple windows 16, 18, 20, and 22 therein. Adjacent each window, decision criteria are set forth. For example, adjacent window 18, the consumer is alerted that he/she should evaluate his/her "Total Cholesterol" relative to the ranges of total cholesterol established as appropriate or inappropriate for treatment with a particular dosage amount of a cholesterol reducing medicine such as MEVACOR® (See FIG. 5). Other decision criteria for selection of MEVACOR® are displayed adjacent to the other windows 16, 20, 22 in package panel 14. For example, next to window 22, the consumer is asked to consider his/her "Gender and Age" as a decision criteria for selection of the medicine. At window 20, the listed decision criteria is "HDL cholesterol" and at window 16, the consumer is asked to consider various health conditions that might negative use of the medicine.

Because the package 10 might not always have its front facing the consumer (as illustrated in FIG. 4), a corresponding upstanding back panel 14' can be used containing windows 16', 18', 20' and 22' whose openings align with corresponding windows 16, 18, 20 and 22. The wording adjacent windows 16', 18', 20' and 22' would preferably be the same as, or similar to, that found on upstanding panel 14 which is illustrated in FIG. 5. Thus, a consumer who finds package 10 on a store shelf with upstanding back panel 14' facing him or her would be directed to the same decision criteria that would be presented to a consumer if the package is oriented as shown in FIG. 4, that is, with back panel 14 rather than 14' facing the consumer.

The windows 16, 18, 20, 22 in panel 14 and windows 16', 18', 20' and 22' in panel 14' frame portions of decision wheels 24, 26, 28 and 30 arranged in a rotating relationship behind, and on, panel 14. Rotation of decision wheels 24, 26, 28 and 30 can be achieved by mounting them on grommets 32 that pass through the center of the decision wheels and are attached to the panel 14 or on a plastic reinforcing member 34 mounted to panel 14 (see FIGS. 3 and 6).

Figure 3:
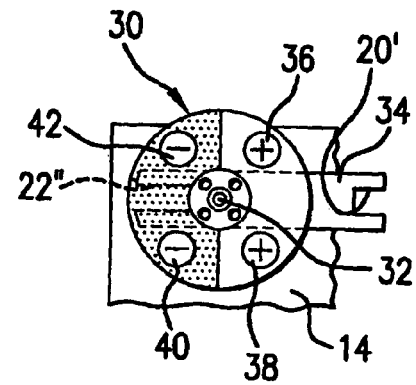
FIG. 3 is a fragmented view similar to FIG. 2 of one decision wheel and means for mounting it on the packaging.

As shown in FIG. 3, decision wheels, 24, 26, 28 and 30 are typically circular in shape and contain selectable responses relating to the decision criteria described above with respect to each of windows 16, 18, 20 and 22. Thus, the decision wheel 30 associated with "Gender and Age" window 22 contains multiple segments indicating positive 36, 38 and negative 40, 42 selectable responses as follows:

| POSITIVE SELECTABLE RESPONSE | NEGATIVE SELECTABLE RESPONSE |
| --- | --- |
| Male, 45 years or older | Male, younger than 45 years |
| Female, 55 years or older | Female, younger than 55 years |

These positive and negative selectable responses on decision wheels 24, 26, 28 and 30 are preferably arranged on both sides of the wheels so that they can be viewed through the windows of both panels 14 and 14'. The distinction between positive and negative portions of the decision wheels is preferably emphasized with color coding and/or symbols. For example, positive selectable responses can be represented by a green coloration, such as a green background behind the response text, and negative selectable responses can be represented by a red coloration, such as a red background behind the response text.

Figure 2:
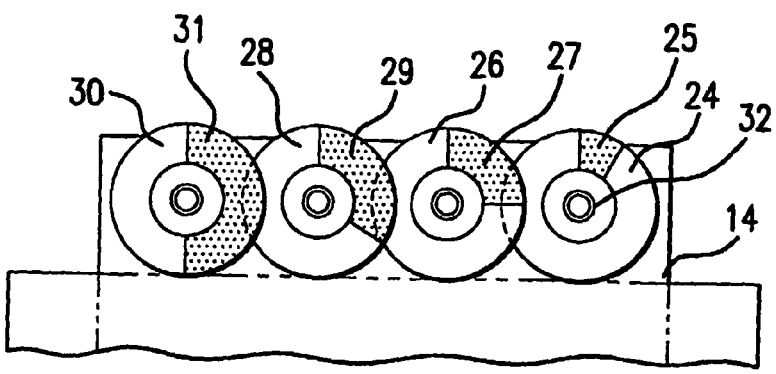
FIG. 2 is a partial rear elevational view of a portion of the interactive packaging of this invention illustrating the decision wheels used in the packaging.

As illustrated in FIG. 2, positive selectable responses are shown as shaded segments 25, 27, 29 and 31 on the respective decision wheels 24, 26, 28 and 30. Any contrasting coloration between positive and negative selectable responses is contemplated by the invention. The selection indicia useable to indicate positive and negative selectable responses are too numerous to list but, for example, a replica of a traffic "Stop" sign can be used as a negative selection indicia to indicate that a particular selectable response is a negative selectable response. That sign coupled with interpretive instructions such as an admonition on the panel 14 or 14', or elsewhere on the package to "Stop and talk to your doctor or pharmacist before buying this product if you see one or more Stop signs" reinforces the negative use message (See FIG. 5).

Other decision criteria associated with additional decision wheels used in the selection of a cholesterol lowering medicine such as MEVACOR® are presented to the consumer on other decision wheels. The decision wheel 26 which is rotatably arranged behind window 18 and 18' illustrates decision criteria based on "total cholesterol" level. The decision wheel 28 which is rotatably arranged behind window 20 illustrates decision criteria for consumers based on their "HDL cholesterol" level. The positive and negative selectable responses associated with each wheel are as follows:

|  | POSITIVE SELECTABLE RESPONSE | NEGATIVE SELECTABLE RESPONSE |
|---|---|---|
| Total Cholesterol | 200–260 mg/dl | Above 260 mg/dl<br>Below 200 mg/dl<br>Don't know, get tested |
| HDL Cholesterol | 1–50 mg/dl | Above 50 mg/dl<br>Don't know, get tested |

The fourth decision wheel 24 in the illustrated embodiment of the invention is rotatably arranged behind window 16 with the legend "Do any of these apply to you?" (See FIG. 5). The decision criteria for this decision wheel is related to pre-existing medical/physical conditions and lifestyle habits, and the decision wheel contains multiple segments that illustrate various characterisitics that would constitute negative selectable responses such as "pregnancy"; "liver disease or hepatitis"; "diabetes"; "stroke"; "heart attack"; "taking other prescriptions," "taking other cholesterol medication," and "consume 3 alcoholic drinks/day." One segment of the decision wheel 24 corresponding in area approximately to the area of the related window 16 would contain positive selection indicia such as coloration or symbols with the legend "None Apply" as the positive selectable response.

A consumer who is about to make a purchase decision would approach a store shelf containing the interactive packaging 10 of this invention. As the consumer approaches, his or her attention would immediately be drawn to the interactive portion of packaging 10. In the illustrated embodiment of this invention, this comprises the upstanding back panel 14 or 14' with a prominent legend containing directive instructions directing the consumer's attention to the decision wheels 24, 26, 28, 30, and inviting the consumer to turn the wheels to determine whether the product is right for them. Interpretive instructions, also presented on the upstanding back panel 14, would advise the consumer how to reach a decision based on the positive and/or negative selection indicia portrayed on the decision wheels through each of the windows once the consumer has selected all his responses from the decision wheels. As illustrated, the interpretive instructions suggest purchase of the consumer product only if all the windows display positive selection indicia (i.e. blue coloration) and consequently positive selectable responses. Conversely, if any of windows 16, 18, 20, 22 or 16', 18', 20', 22' display negative selection indicia (i.e. yellow coloration) and consequently negative selectable responses, the consumer is advised not to buy the product, unless and until he or she has consulted a doctor or pharmacist.

To reinforce that invitation, instructional closure flaps 44, 46 can optionally be included as part of package 10. These flaps 44, 46 are inserted in corresponding slots 48, 50 of package 10 when assembled (See FIGS. 1, 4). Flaps 44, 46 are preferably printed in a bright color that contrasts with the coloration on the balance of package 10 so that they attract the attention of a consumer as he or she approaches the package 10 on a store shelf. Writing on tabs 44, 46 instruct the consumer not to pull tabs 44, 46 out of slots 48, 50 to open the package 10 until after using the decision wheels. The instruction on tabs 44, 46 is designed to focus the consumer purchasing decision on the interactive aspect of the packaging, namely, the decision wheels and associated printing on panels 14 or 14'.

It is certainly contemplated that in other forms of this embodiment comprising interactive packaging with decision wheels that other numbers and forms of decision wheels could be used. While four such wheels are illustrated, any number of wheels could be used to aid the consumer purchasing decision. In a similar vein, it is not necessary that the purchasing decision be dependent upon the consumer's unanimous selection of positive selectable responses when rotating the decision wheels. The interpretive instructions could establish purchase criteria based on positive responses to less than all of the decision wheels.

The invention has been illustrated by detailed description and examples of the preferred embodiment. Various changes in form and detail will be within the skill of persons skilled in the art. Therefore, the invention must be measured by the claims and not by the description of the examples or the preferred embodiments. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. Interactive packaging for a consumer product wherein the product is appropriate for less than all consumers comprising:
   (a) an enclosure for the product;
   (b) at least one manipulatable product selection device integrated with the enclosure, wherein each product selection device is comprised of:
      (i) a display of decision criteria that are relevant to appropriate selection or deselection of the product,
      (ii) a display of at least two selectable responses associated with each decision criteria, wherein there is at least one positive selectable response and at least one negative selectable response for each decision criteria, and
      (iii) a display of selection indicia associated with each selectable response, wherein positive selection indicia is associated with each positive selectable response and negative selection indicia is associated with each negative selectable response;
   (c) directive instructions displayed on the enclosure which direct an operator to manipulate each product selection device to choose a consumer applicable response from the available selectable responses per decision criteria; and
   (d) interpretive instructions displayed on the enclosure which explain how to interpret the pattern of selection indicia which is associated with the chosen one or more consumer applicable responses to assist with determining whether or not the product is appropriate for the consumer's purchase or use, wherein a decision wheel displays the selectable responses and their associated selection indicia, wherein there is one decision wheel associated with each display of decision criteria, and wherein the decision wheel is rotatably mounted on a portion of the enclosure, and wherein the interactive packaging further comprises one window in a portion of the enclosure for each decision wheel, wherein the window overlays a portion of the decision wheel and is aligned with the decision wheel so as to be capable of visually exposing one entire selectable response and its associated selection indicia at a time when the wheel is rotated.

2. The interactive packaging of claim 1 wherein the enclosure is a box or carton.

3. The interactive packaging of claim 1 wherein an opposite pair of selection indicia comprised of one positive selection indicia and one negative selection indicia is employed, wherein the positive selection indicia is repeatedly associated with each of the positive selectable responses and the negative selection indicia is repeatedly associated with each of the negative selectable responses.

4. The interactive packaging of claim 3 wherein the opposite pair of selection indicia comprised of a first symbol selected from an alphanumeric graphic, a pictorial graphic, a color and combinations thereof as the positive selection indicia, and a second, different symbol selected from an alphanumeric graphic, a pictorial graphic, a color and combinations thereof as the negative selection indicia.

5. The interactive packaging of claim 4 wherein the opposite pair of selection indicia is comprised of a first color as the positive selection indicia and a second, different color as the negative selection indicia.

6. The interactive packaging of claim 3 wherein the opposite pair of selection indicia is comprised of a first color as the positive selection indicia and a second, different color as the negative selection indicia.

7. The interactive packaging of claim 1 comprised of at least two product selection devices.

8. The interactive packaging of claim 7 comprised of from two to six product selection devices.

9. The interactive packaging of claim 1 wherein the consumer product is an OTC pharmaceutical.

10. The interactive packaging of claim 9 wherein the OTC pharmaceutical is selected from alendronate sodium and oxybutynin chloride.

11. The interactive packaging of claim 9 wherein the OTC pharmaceutical is a lipid management drug.

12. The interactive packaging of claim 11 wherein the decision criteria displayed for each product selection device is selected from the group consisting of gender, age, total cholesterol level, low-density lipoprotein cholesterol level, high density lipoprotein cholesterol level, pre-existing physical and medical conditions, concurrent medication usage, alcohol intake over a specified period of time and combinations thereof.

13. The interactive packaging of claim 11 wherein the lipid management drug is an HMG-CoA reductase inhibitor.

14. The interactive packaging of claim 13 wherein the HMG-CoA reductase inhibitor is selected from the group consisting of lovastatin, simvastatin, pravastatin, atorvastatin, fluvastatin, cerivastatin and the pharmaceutically acceptable salts thereof.

15. The interactive packaging of claim 14 wherein the HMG-CoA reductase inhibitor is lovastatin.

16. The interactive packaging of claim 15 wherein the HMG-CoA reductase inhibitor is simvastatin.

* * * * *